(12) United States Patent
Sarma et al.

(10) Patent No.: US 9,234,248 B2
(45) Date of Patent: Jan. 12, 2016

(54) **SIMULTANEOUS QUANTITATIVE MULTIPLE PRIMER DETECTION OF *CLOSTRIDIUM DIFFICILE***

(75) Inventors: Aartik Sarma, Brookline, MA (US); Anubhav Tripathi, Northboro, MA (US); Leonard Mermel, Barrington, RI (US); Aleksey Novikov, Providence, RI (US); Leah Seward, North Attleboro, MA (US); Jennifer Fieber, Tucson, AZ (US)

(73) Assignee: Brown University, Providence, RI (US)

( * ) Notice: Subject to any disclaimer, the term of this patent is extended or adjusted under 35 U.S.C. 154(b) by 786 days.

(21) Appl. No.: 13/384,446

(22) PCT Filed: Jul. 15, 2010

(86) PCT No.: PCT/US2010/042121
§ 371 (c)(1),
(2), (4) Date: Jun. 22, 2012

(87) PCT Pub. No.: WO2011/008942
PCT Pub. Date: Jan. 20, 2011

(65) Prior Publication Data
US 2012/0252029 A1   Oct. 4, 2012

Related U.S. Application Data

(60) Provisional application No. 61/226,453, filed on Jul. 17, 2009, provisional application No. 61/263,908, filed on Nov. 24, 2009.

(51) Int. Cl.
*C12Q 1/68* (2006.01)
(52) U.S. Cl.
CPC ............ *C12Q 1/689* (2013.01); *C12Q 2600/16* (2013.01)
(58) Field of Classification Search
None
See application file for complete search history.

(56) References Cited

U.S. PATENT DOCUMENTS

2009/0203021 A1   8/2009   Cockerill, III et al.
2009/0208948 A1   8/2009   Paquette et al.

FOREIGN PATENT DOCUMENTS

NL   WO2010/116920   * 10/2010   ............... C12Q 1/68
WO   WO2009030031 A1   3/2009

OTHER PUBLICATIONS

Lowe et al. (Nucleic Acids Research, 1990, 18(7):1757-1761).*
Lemee et al., "Multilocus sequence analysis and comparative evolution of virulence-associated genes and housekeeping genes of *Clostridium difficile*", Microbiol. Oct. 2005, vol. 151, pp. 3171-3180.
GenBank: DQ117049.1, *Clostridium difficile* strain FM18 CdtB (cdtB) gene; partial cds, Oct. 2005, http://www.ncbi.nlm.nih.gov/nuccore/DQ117049, nucleotides 305-324.
Bouvet et al., Genetic Relatedness of *Clostridium difficile* Isolates from Various Origins Determined by Triple-Iocus Sequence Analysis Based on Toxin Regulatory Genes tcdC, tcdR, and cdtR, J. Clin. Microbiol., Nov. 2008, vol. 46, No. 11, pp. 3703-3713.
PCT/US2010/042121 International Search Report dated Jan. 6, 2011.
Lyerly et al., "*Clostridium difficile*: its disease and toxins", Clin. Microbiol. Rev. 1988, 1(1):1. DOI: 10.1128/CMR.1.1.1., pp. 1-18.
Voth et al., "*Clostridium difficile* Toxins: Mechanisms of Action and Role in Disease", Clin. Micorbiol. Rev. 2005, 18(2):247. DOI:10.1128/CMR.18.2.247-263.2005.
Rupnik et al., "Revised Nomenclature of *Clostridium difficile* Toxins and Associated Genes", Journal of Medical Microbiology (2005), 54, 113-117.
Zheng et al., "Multicenter Evaluation of a New Screening Test That Detects *Clostridium difficile* in Fecal Specimens", Journal of Clinical Microbiology, vol. 42, No. 8, Aug. 2004, pp. 3837-3840.

* cited by examiner

*Primary Examiner* — Stephanie K Mummert
(74) *Attorney, Agent, or Firm* — Novak Druce Connolly Bove + Quigg LLP

(57) ABSTRACT

This invention comprises a multiplex-capable oligonucleotide which is capable of hybridizing to at least one of the *C. difficile* tcdB, tcdC, or cdtB genes, wherein, wherein said primer consists of a sequence selected from the group consisting of SEQ ID NOS: 1 through 9, or a sequence that exhibits no more than one substitution of a base to a sequence selected from the group consisting of SEQ ID NOS: 1 through 9 and method for polymerase chain reaction (PCR) determining of the presence of a toxigenic strain of *C. difficile* in a biological sample utilizing said probes.

17 Claims, 3 Drawing Sheets

SIMULTANEOUS QUANTITATIVE MULTIPLE PRIMER DETECTION OF *CLOSTRIDIUM DIFFICILE*

CROSS REFERENCE TO RELATED APPLICATION

This application is a national phase application of, and claims priority to, PCT/US2010/042121, filed on Jul. 15, 2010, which claims priority under 35 U.S.C. §119(e) of U.S. provisional application Ser. No. 61/226,453 filed Jul. 17, 2009 and U.S. provisional application Ser. No. 61/263,908 filed Nov. 24, 2009, the disclosures of which are incorporated herein by reference in their entirety.

STATEMENT OF GOVERNMENT RIGHTS

This invention was made with government support under National Science Foundation, Grant BES-0555874. The government has certain rights in the invention.

SEQUENCE LISTING

The instant application contains a Sequence Listing which has been submitted via EFS-Web and is hereby incorporated by reference in its entirety. Said ASCII copy, created on Aug. 17, 2010, is named B0197015.txt and is 2,633 bytes in size.

FIELD OF THE INVENTION

This invention comprises a multiplex-capable oligonucleotide primer which is capable of hybridizing to at least one of the *C. difficile* tcdB, tcdC, or cdtB genes, wherein, wherein said primer consists of a sequence selected from the group consisting of SEQ ID NOS: 1 through 9, or a sequence that exhibits no more than one substitution of a base to a sequence selected from the group consisting of SEQ ID NOS: 1 through 9 and method for polymerase chain reaction (PCR) determining of the presence of a toxigenic strain of *C. difficile* in a biological sample utilizing said probes.

BACKGROUND OF THE INVENTION

*Clostridium difficile* is a common identified cause of antibiotic associated diarrhea, accounting for 15%-25% of cases (Bartlett, 1994, Clin. Infect. Dis., 18 (Suppl 4): S265-272). A more severe form of CDI has been identified. Many cases of this severe form of CDI have been shown to be caused by an "epidemic" strain of *C. difficile*, which has been characterized as "BI" by restriction enzyme analysis (REA), "NAP1" (North American Pulsed Field Type 1) by pulsed field gel electrophoresis, and "027" by PCR ribotyping. In addition, it has been characterized as "toxinotype III" (by REA of toxin genes). In prior years, the great majority of "non-epidemic" hospital strains of *C. difficile* belonged to toxinotype 0. This BI/NAP1/027 "epidemic" strain has been shown to be a hyperproducer of toxins A and B, to which is attributed the increased virulence of the epidemic strain. The tcdC gene, within the pathogenicity locus of the "epidemic" strain, appears to be a negative regulator of toxin A and B production.

Toxigenic strains of *C. difficile* commonly produce two large toxins, an enterotoxin; toxin A (TcdA) and a cytotoxin; toxin B (TcdB), to which disease symptoms are attributed. Without being bound by any particular theory, it is believed that these toxins are expressed efficiently during growth of *C. difficile* in response to an environmental stimulus. Their activities modulate numerous physiological events in the cell and are believed to contribute directly to disease. In humans the two toxins have been associated with pseudomembranous colitis and antibiotic associated diarrhea. Reported transmission occurs primarily in health care facilities, where exposure to antimicrobial drugs and environmental contamination by *C. difficile* spores are common.

Without being bound by any particular theory, it is believed that toxin A and toxin B are encoded by genes tcdA and tcdB. Both have been sequenced and are reportedly found in single open reading frames. Together with three additional genes (tcdC, tcdD, tcdE), they are reported to form a 19.6 kb chromosomal pathogenicity locus (Paloc) (8). Both open reading frames are large, with tcdA spanning a reported 8,133 nucleotides and tcdB being reported as 7,098 nucleotides in length. It is further believed that *C. difficile* toxigenic strains produced both toxin A and toxin B whereas nontoxigenic strains lacked both toxins (Rupnik et al. supra.; Lyerly et al., Clin. Micro. Rev., 1998, Jan. 1-18). Toxigenic reference strain VP1 10463 is an example of a strain producing TcdA and TcdB.

In determining the toxicity of a *C. difficile* strain, rapid determination is a central concern. If multiplex PCR can be applied, the process of determining the toxicity of a *C. difficile* strain will be radically improved. Multiplex PCR is a variant of PCR which enabling simultaneous amplification of many targets of interest in one reaction by using more than one pair of primers. Reported uses include genotyping applications where simultaneous analysis of multiple markers is required. It is also used in detection of pathogens. However, multiplex assays can be tedious and time-consuming to establish, requiring lengthy optimization procedures. Note is made of *Clostridium difficile* Toxins: Mechanism of Action and Role in Disease, Voth et al., *Clinical Microbiology Reviews*, (18)$_2$: 247-263 (2005), the teachings of which are incorporated herein by reference.

Optimization of a determination of *C. difficile* type requires particular attention to many factors including primer design/selection, annealing temperature and extension time and temperature. Noted considerations in primer selection include selecting the length of individual primers, primer melting temperature and differential melting temperatures of all primers, purine:pyrimidine content; and degree of primer-primer interactions.

A related optimization issue is the adjusting of cycling conditions and buffer concentrations required for each primer pair. Annealing temperature is also a significant concern with unduly low annealing temperatures associated with the appearance of unspecific secondary products. Establishing an extension time is a significant consideration. The given of multiplex PCR is with more loci simultaneously amplified, then the pool of enzyme and nucleotides may become a key limiting factor. Thus, determination of time necessary for the polymerase molecules to complete synthesis is useful.

Reference is made to Rupnik, M. et al., J. Med. Microbiol, 2005, 54: 113-117; Voth, D. E. et al., Clinical Microbiol. Reviews, 2005, 18: 247-263; U.S. Pub. No. 20090208948 to Paquette et al., and U.S. Pub. No. 20090203021 to Cockerill et al., the teachings of which are incorporated herein by reference in their entirety as are all publications cited herein.

SUMMARY OF THE INVENTION

This invention comprises a multiplex-capable oligonucleotide which is capable of hybridizing to at least one of the *C. difficile* tcdB, tcdC, or cdtB genes, wherein, wherein said oligonucleotide consists of a sequence selected from the group consisting of SEQ ID NOS: 1 through 9, or a sequence that exhibits no more than one substitution of a base to a sequence selected from the group consisting of SEQ ID NOS: 1 through 9.

This invention further comprises a method for polymerase chain reaction (PCR) determining of the presence of a toxigenic strain of *C. difficile* in a biological sample, comprising:
 a. simultaneously contacting said biological sample with at least three pairs of multiplex-capable oligonucleotides each of claim 1;
 b. amplifying target nucleic acid from said biological sample; and,
 c. detecting the presence or amount of an amplified product(s) as an indicator of the presence of said toxigenic strain of *C. difficile* in said biological sample.

In particular embodiments of this method the biological sample is selected from the group consisting of stool, sputum, peripheral blood, plasma, serum, lymph nodes, respiratory tissue and exudates. In some embodiments the PCR is selected from the group consisting of AFLP, Alu-PCR, Asymmetric PCR Colony PCR, DD-PCR, Degenerate PCR, Hotstart PCR, In situ PCR, Inverse PCR Long-PCR, Multiplex PCR, Nested PCR, PCR-ELISA, PCR-RFLP, PCR-single strand conformation polymorphism (PCR-SSCP), quantitative competitive PCR (QC-PCR), rapid amplification of cDNA ends-PCR(RACE-PCR), Random Amplification of Polymorphic DNA-PCR(RAPD-PCR), Real-Time PCR, Repetitive extragenic palindromic-PCR (Rep-PCR), reverse transcriptase PCR(RT-PCR), TAIL-PCR, Touchdown PCR and Vectorette PCR with particular reference to quantitative real-time PCR (QRT-PCR).

DETAILED DESCRIPTION OF THE INVENTION

Figure 1:
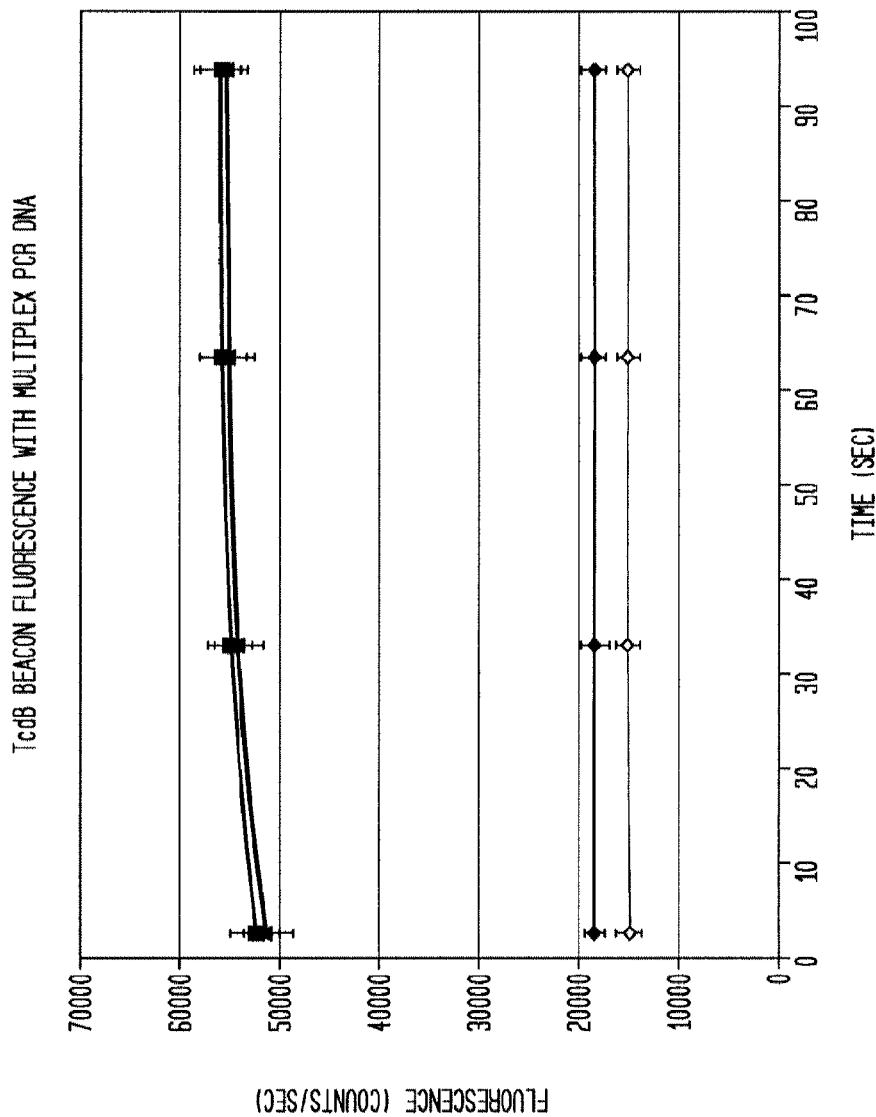
FIG. 1 is a plot of TcdB beacon flouresence with multiplex PCR DNA. In all four conditions, solutions contained 10 nM beacon and 6.00 mM MgCl. Fluorescence measurements were taken at 55° C. for 120 seconds. Square data points (■) depict the fluorescent signal emitted by the beacon when combined with multiplex DNA amplified from clinical sample 8. Triangular data points (Δ) represent the fluorescence emitted by the beacon when in solution with multiplex DNA amplified from clinical sample 3. Diamond data points (♦) correspond to the fluorescent signal produced when non-target DNA was added to the sample. Circular data points (●) indicate the background signal of the beacon alone in the buffer solution.
Figure 2:
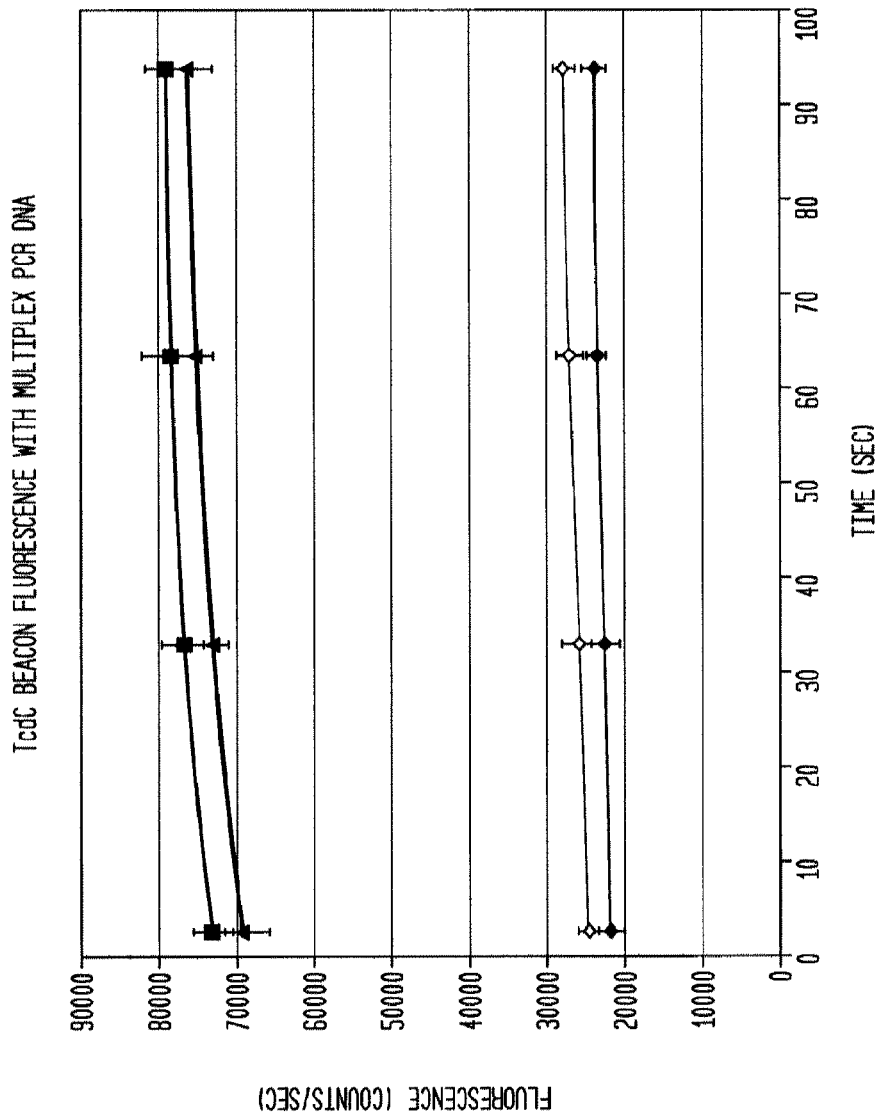
FIG. 2 is a plot of TcdC beacon fluorescence with multiplex PCR-amplified DNA. In all four conditions, solutions contained 10 nM beacon and 6.00 mM MgCl. Fluorescence measurements were taken at 55° C. for 120 seconds. Square data points (■) depict the fluorescent signal emitted by the beacon when combined with multiplex DNA amplified from clinical sample 8. Triangular data points (Δ) represent the fluorescence emitted by the beacon when in solution with multiplex DNA amplified from clinical sample 3. Diamond data points (♦) correspond to the fluorescent signal produced when non-target DNA was added to the sample. Circular data points (●) indicate the background signal of the beacon alone in the buffer solution.
Figure 3:
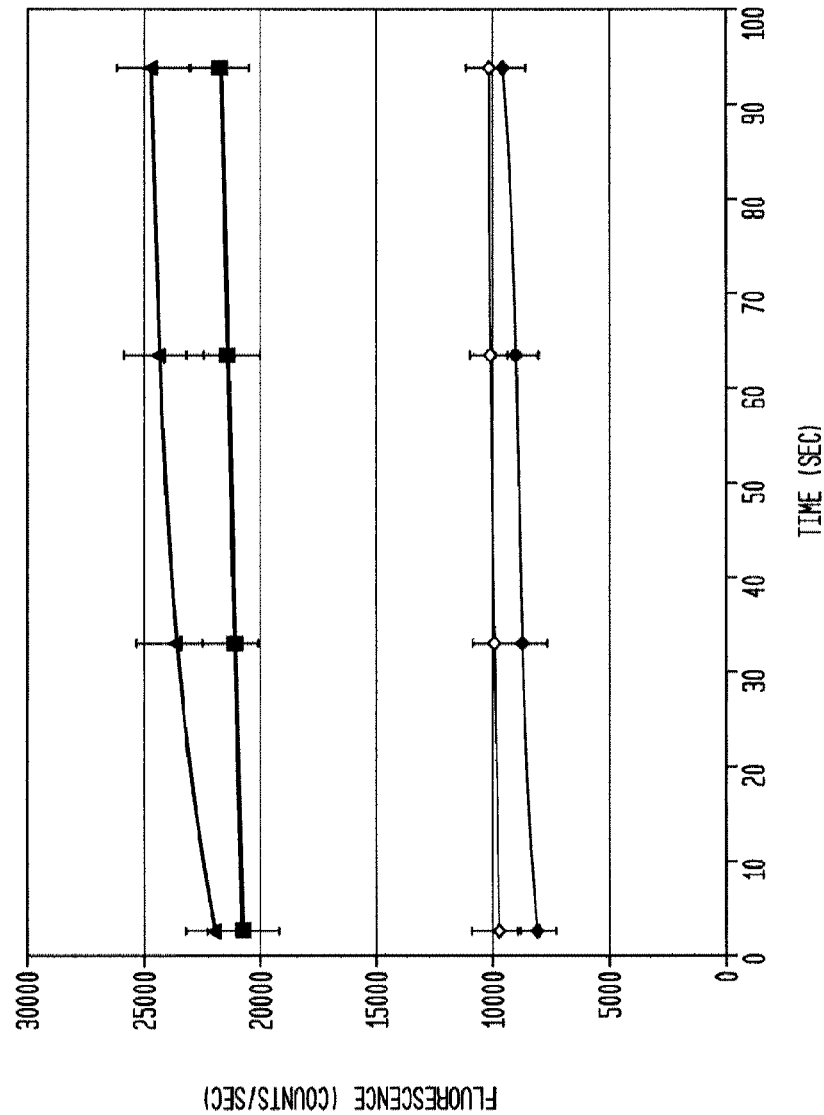
FIG. 3 is a plot of CdtB beacon fluorescence with multiplex PCR-amplified DNA. In all four conditions, solutions contained 10 nM beacon and 6.00 mM MgCl. Fluorescence measurements were taken at 55° C. for 120 seconds. Square data points (■) depict the fluorescent signal emitted by the beacon when combined with multiplex DNA amplified from clinical sample 8. Triangular data points (Δ) represent the fluorescence emitted by the beacon when in solution with multiplex DNA amplified from clinical sample 3. Diamond data points (♦) correspond to the fluorescent signal produced when non-target DNA was added to the sample. Circular data points (●) indicate the background signal of the beacon alone in the buffer solution.

The described process can be used to rapidly and sensitively detect the presence of *Clostridium difficile* using a single reaction tube. In addition, the procedure described can identify various mutations in the bacterial genome that correspond to clinically relevant markers of pathogenicity—specifically, the presence of an 18 bp deletion in the regulatory tcdC gene, which is associated with a hypervirulent strain of the bacteria, and the presence of a binary toxin gene that is also present in emerging strains of *C. difficile*.

This invention will be better understood with reference to the following definitions.

(a) "Multiplex-capable" shall mean a reaction that can sensitively and selectively amplify at least 3 amplicons from a sample in a single reaction mixture if they are present in the original sample, while non-specific products should not make more than about 10% (w/w) of the DNA synthesized in tubes containing the target genes.

In this context, sensitively shall be understood to mean detect the presence of an oligonucleotide of the invention at least about 70% of the time and in some embodiments at least about 80% of the time, and preferably about 90% of the time, with particular reference to about 95% of the time and about 99% of the time. Selectively is a determination of the number of true negatives divided by the number of true negatives+the number of true positives. Expressed as a percentage, selective will be understood to mean about 90% of the time, with particular reference to about 95% of the time and about 99% of the time.

(b) "Primer" shall mean an oligonucleotide sequence that is designed to hybridize with a complementary portion of a target sequence, a probe, or a ligation product, and undergo primer extension. In the practice of this invention complimentarity is a significant attribute. Non-complimentarity of the nucleotides within the primer will greatly lower sensitively. In the practice of this invention, suitable primers have no more than one substitution base. Adding or subtracting bases from the ends of the primers will change the annealing temperatures. Annealing temperatures for multiplex runs are optimal if they are no more than about 1.5° C. disparity for all primers.

(c) In some instances, Primers are called probes. "Probe" are nucleic acid oligomers that hybridize specifically to a target sequence in a nucleic acid, under conditions that allow hybridization, thereby allowing detection of the target or amplified nucleic acid. The probe's "target" generally refers to a sequence within or a subset of an amplified nucleic acid sequence which hybridizes specifically to at least a portion of a probe oligomer by standard hydrogen bonding (i.e., base pairing). A probe may comprise target-specific sequences and other sequences that contribute to three-dimensional conformation of the probe.

In the practice of this invention, primers and/or probes are utilized to permit amplification of a *C. difficile* nucleic acid template containing a tcdB-derived target nucleotide sequence and to optionally introduce additional features into the amplification products. Each primer and/or probe contains a nucleotide sequence that is complementary to a region of target nucleotide sequence in the template, in order for each primer to bind (anneal) to the template.

(d) "Clinical sample" shall mean any tissue or excreta which may contain *C. difficile* nucleic acid, including, for example, stools (liquid or soft), sputum, peripheral blood, plasma, serum, biopsy tissue including lymph nodes, respiratory tissue or exudates, or other body fluids, tissues or materials. In some embodiments, a clinical sample is treated to physically, chemically and/or mechanically disrupt tissue or cell structure or consistency, thus releasing or freeing clinical sample components such as intracellular components. It is contemplated that in some embodiments, clinical sample preparation uses a solution that contains buffers, salts, detergents and the like which are used to prepare the sample for analysis.

In one embodiment, DNA isolated from clinical stool samples using existing commercial kits are be added to a prepared 50 ul solution containing 5 ul 10× Taq polymerase buffer concentrate (New England Biosciences), six primers that specifically target three genes—tcdB, tcdC, and cdtB—found in the *Clostridium difficile* genome (0.167 uM each tcdB primer, 0.267 uM each tcdC primer, 0.267 uM each cdtB primer), 5 nM each of 3 dual-labeled probes ("molecular beacons") each corresponding to one of the three target genes listed above that fluoresce in the presence of DNA amplified from their respective target gene, 0.2 mM each ATP, CTP, GTP, and TTP, 0.1 U/ul Taq polymerase, 0.1 ug/ul bovine serum albumin, and 6 mM magnesium chloride. The primers were designed by aligning known sequences of *Clostridium difficile* samples and identifying regions of limited mutation. Within these regions, primers (single-stranded short DNA fragments required to initiate replication of DNA in vitro) with good binding energy were designed to specifically amplify DNA sequences by the polymerase chain reaction. The primer sequences are listed below, and are named by the gene they amplify; the FWD and REV suffixes identify the strand of the double-stranded DNA (dsDNA) fragment to which the primer binds. The primers, synthesized by Integrated DNA Technologies (IDT), Coralville, Iowa, are listed below by SEQ ID NO:

```
SEQ ID NO:cdtBFWD   5' - GCA GTT AAG TGG GAA GAT
1                        AG - 3'

SEQ ID NO:cdtBREV   5' - TCC ATA CCT ACT CCA ACA
2                        AT - 3'

SEQ ID NO:tcdBFWD   5' - CTG GAG AAT CTA TAT TTG
3                        TAG - 3'

SEQ ID NO:tcdBREV   5' - GCA GTT AAG TGG GAA GAT
4                        AG - 3'

SEQ ID NO:tcdCFWD   5' - CTC AAA AAA CAG AAA TAG AAA
5                        C - 3'

SEQ ID NO:tcdCREV   5' - ACC TCA TCA CCA TCT TC - 3'
6

SEQ ID NO:tcdB      5' - 6-FAM/CGC GAT TGA TAC TGT AA
7                        TGG TAA GTT TCG CG/IABLFQ - 3'

SEQ ID NO:tcdC      5' - TEX/CGT GCT AAA AAG GCT GAA
8                        GAA CAA CGC ACG/IABLRQ - 3'

SEQ ID NO:cdtB      5' - Cy5/CGT GTC TTT AGA GTC AAA
9                        TAC TGC TGG ACA CG/IABLRQ - 3'
```

Note that #6, above, overlaps SEQ ID NO:1 as disclosed in US2009/0203201 to Cockerille (U.S. Ser. No. 12/367,014) (5'-ACC TCA TCA CCA TCT TCA ATA AC-3' (SEQ ID NO: 10))—but is 6 bases shorter. Primer design for multiplex-capable reactions requires optimizing the sensitivity and specificity for the target genes while minimizing the binding energy of a primer binding to another primer in the system. The longer primer, SEQ ID NO:1 from US2009/0203201, which includes the sequence of tcdCREV, has a greater binding energy (is more negative) to other primers in the system and is unsuitable for the present system. Primers of the present invention are less negative; that is closer to 0 binding energy.

Molecular beacons as used in the present invention are single-stranded sequences of DNA that form a closed hairpin structure; the ends of each sequence are labeled with a fluorophore that emits light of a specific wavelength when excited by an appropriate wavelength and a quencher molecule that absorbs light emitted by the fluorophore. In the absence of its complementary target sequence, the beacon adopts a closed hairpin structure, a conformation which effectively prevents detection of fluorescence. In the presence of a sequence complementary to the hairpin loop, the beacon binds to its target, thereby separating the fluorophore from the quencher and allowing detection of light. By using different fluorophores, it is possible to distinguish the presence of various gene sequences in a solution. The three target sequences were selected because they are highly conserved in published *C. difficile* sequences. TcdB detects the gene encoding *C. difficile* Toxin B, the standard target of the enzyme immunoassay used to verify the presence of *C. difficile* in hospitals. CdtB detects a gene encoding part of an emerging binary toxin that has been observed in some strains of *C. difficile*. Finally, tcdC detects strains of *C. difficile* that have an 18 bp deletion in a regulatory gene which is associated with an emerging hypervirulent strain. The following beacons (IDT) are used to detect the presence of these clinically relevant markers:

```
                                              (SEQ ID NO: 7)
tcdB - 5' - 6-FAM/CGC GAT TGA TAC TGT AA TGG TAA
GTT TCG CG/IABLFQ - 3'

(SEQ ID NO: 8)
tcdC - 5' - TEX/CGT GCT AAA AAG GCT GAA GAA CAA
CGC ACG/IABLRQ - 3'

(SEQ ID NO: 9)
cdtB - 5' - Cy5/CGT GTC TTT AGA GTC AAA TAC TGC
TGG ACA CG/IABLRQ - 3'
```

6-FAM is a fluorescent dye that emits light at 520 nm; TEX is a fluorescent dye that emits light at 613 nm; Cy5 is a fluorescent dye that emits light at 668 nm; IABLFQ and IABLRQ are fluorescence quenchers that absorb light from 420-620 nm and 500-700 nm respectively.

Presence of *C. difficile* DNA in clinical samples is verified using a pair of PCR primers for the *C. difficile* gluD gene first reported as "Multicenter Evaluation of a New Screening Test That Detects *Clostridium difficile* in Fecal Specimens," Zheng, et al., *Journal of Clinical Microbiology*, 42(8) 3837-3840 (2004). As reported, their procedure curtailed non-specific signals observed on am Agilent DNA 7500 microfluidic gel electrophoresis chip. Also useful is the Agilent 2100 Bioanalyzer.

In one embodiment, a 0.2 ml polypropylene PCR tube containing the reaction mixture is placed in a thermal cycling apparatus using the following heating protocol:
Initial denaturation: 5 min at 94° C.

Amplification (40 cycles):
30 sec at 94° C.
30 sec at 61° C. to 53° C., decreasing by 0.5° C. per cycle
1 min at 72° C.
Final extension: 10 min at 72° C.

After amplification, the sealed tube is placed in a fluorometer for quantification of the signal, or observed by visual inspection while excited by a light source to qualitatively determine the presence of the three target genes, based on the color of the emitted light.

Since the probes have different colored fluorophores, it's possible to discriminate between the behaviors of each probe in a solution as long as the equipment being used can tell the difference. In some embodiments it is useful to discriminate between probes by determining the melting temperature between one or both of said tcdC probe(s) and said tcdC amplification product, wherein said melting temperature confirms said presence or said absence of said *C. difficile*.

Example 1

Stool Processing for PCR

A swab was inserted into a clinical sample of stool at various locations and swirled into a tube containing 1 ml of sterile water (approximately 1:10 stool dilution) and allowed to settle. Two hundred microliters of the supernatant was placed into a sample cartridge for DNA extraction using the MagNA Pure system with the MagNA Pure LC Total Nucleic Acid Isolation Kit.

Example 2

Multiflex Amplification by PCR

DNA isolated from clinical stool samples using existing commercial kits (Example 1) are added to a prepared 50 ul solution containing 5 ul 10× Taq polymerase buffer concentrate (New England Biosciences), six primers that specifically target three genes—tcdB, tcdC, and cdtB—found in the *Clostridium difficile* genome (0.167 uM each tcdB primer, 0.267 uM each tcdC primer, 0.267 uM each cdtB primer), 5 nM each of 3 dual-labeled probes ("molecular beacons") each corresponding to one of the three target genes listed above that fluoresce in the presence of DNA amplified from their respective target gene, 0.2 mM each ATP, CTP, GTP, and TTP, 0.1 U/ul Taq polymerase, 0.1 ug/ul bovine serum albumin, and 6 mM magnesium chloride. A 0.2 ml polypropylene PCR tube containing the reaction mixture is placed in a thermal cycling apparatus using the following heating protocol:
Initial denaturation: 5 min at 94° C.

Amplification (40 cycles):
30 sec at 94° C.
30 sec at 61° C. to 53° C., decreasing by 0.5° C. per cycle
1 min at 72° C.
Final extension: 10 min at 72° C.

Example 3

Interpreting Results

The reaction product is evaluated for the presence of the target amplicons using fluorescent hairpin probes described above. In the presence of the target amplicon a probe opens and fluorescence is observed and measured. With the use of differently colored fluorophores, the presence of multiple amplicons is assessed in the same tube without requiring further purification. Measurement is accomplished by exciting the fluorophores with the appropriate wavelength of light and then collecting light of the appropriate emission wavelength. In some embodiments, amplification of each gene product is evaluated using gel electrophoresis to separate the amplicons and then observing the sizes of the amplicons using fluorescent imaging by staining with a nucleic-acid-specific stain such as ethidium bromide. Thus, with 3 amplicons, the result is three bands. In the present example, the presence of each gene can be verified by size separation by gel electrophoresis and visualization by ethidium bromide or a similar nucleotide-specific dye. Up to three bands corresponding to product lengths of approximately 150, 300, and 350 base pairs will verify the presence of the cdtB, tcdC, and tcdB genes, respectively. If a gene is not present or there is a false negative result there will be fewer bands.

Results of fluorescence measurements show that each of the three beacons designed in the study produced higher fluorescent signals when in the presence of multiplex PCR-amplified DNA containing the target gene than when in the presence of amplified DNA that lacked the target gene. In addition, the fluorescence emissions for the two negative control conditions tested in each trial, beacon in buffer solution which signifies the beacon's background fluorescent signal and beacon with non-target DNA, were quite similar. Such results indicate that each of the molecular beacons bound its respective target with high specificity.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A multiplex-capable oligonucleotide which is capable of hybridizing to at least one of the *C. difficile* tcdB, tcdC, or cdtB genes, wherein said oligonucleotide consists of a sequence including at least two primers selected from the group consisting of SEQ ID NOS: 1 through 9, or a sequence that exhibits no more than one substitution of a base to a sequence selected from the group consisting of SEQ ID NOS: 1 through 9, wherein one said primer is a synthetic primer selected from the group of SEQ ID NOS: 7, 8, or 9.

2. The multiplex-capable oligonucleotide of claim 1 consisting of SEQ ID NO 1 and SEQ ID NO: 7.

3. The multiplex-capable oligonucleotide of claim 1 consisting of SEQ ID NO 2.

4. The multiplex-capable oligonucleotide of claim 1 consisting of SEQ ID NO 3.

5. The multiplex-capable oligonucleotide of claim 1 consisting of SEQ ID NO 4.

6. The multiplex-capable oligonucleotide of claim 1 consisting of SEQ ID NO 5.

7. The multiplex-capable oligonucleotide of claim 1 consisting of SEQ ID NO 6.

8. The multiplex-capable oligonucleotide of claim 1 consisting of SEQ ID NO 7.

9. The multiplex-capable oligonucleotide of claim 1 consisting of SEQ ID NO 8.

10. The multiplex-capable oligonucleotide of claim 1 consisting of SEQ ID NO 9.

11. A method for polymerase chain reaction (PCR) determining of the presence of a toxigenic strain of *C. difficile* in a biological sample, comprising:

a. simultaneously contacting said biological sample with at least three pair of multiplex-capable oligonucleotides each of claim 1;
b. amplifying target nucleic acid from said biological; and,
c. detecting the presence or amount of an amplified product(s) as an indicator of the presence of said toxigenic strain of *C. difficile* in said biological sample.

12. The method of claim 11, wherein said biological sample is selected from the group consisting of stool, sputum, peripheral blood, plasma, serum, lymph nodes, respiratory tissue and exudates.

13. The method of claim 12, wherein said biological sample is a stool sample.

14. The method of claim 11, wherein said PCR is selected from the group consisting of AFLP, Alu-PCR, Asymmetric PCR Colony PCR, DD-PCR, Degenerate PCR, Hot-start PCR, In situ PCR, Inverse PCR Long-PCR, Multiplex PCR, Nested PCR, PCR-ELISA, PCR-RFLP, PCR-single strand conformation polymorphism (PCR-SSCP), quantitative competitive PCR (QC-PCR), rapid amplification of cDNA ends-PCR(RACE-PCR), Random Amplification of Polymorphic DNA-PCR (RAPD-PCR), Real-Time PCR, Repetitive extragenic palindromic-PCR (Rep-PCR), reverse transcriptase PCR (RT-PCR), TAIL-PCR, Touchdown PCR and Vectorette PCR.

15. The method of claim 14, wherein said PCR is quantitative real-time PCR (QRT-PCR).

16. The multiplex-capable oligonucleotide of claim 1 consisting of SEQ ID NO 1 and SEQ ID NO: 8.

17. The multiplex-capable oligonucleotide of claim 1 consisting of SEQ ID NO 1 and SEQ ID NO: 9.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcagttaagt gggaagatag                                                20
```

-continued

```
<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tccataccta ctccaacaat                                                 20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctggagaatc tatatttgta g                                               21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcagttaagt gggaagatag                                                 20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcaaaaaac agaaatagaa ac                                              22

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acctcatcac catcttc                                                    17

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgcgattgat actgtaatgg taagtttcgc g                                    31

<210> SEQ ID NO 8
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgtgctaaaa aggctgaaga acaacgcacg                                    30

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgtgtcttta gagtcaaata ctgctggaca cg                                 32

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acctcatcac catcttcaat aac                                           23
```